(12) United States Patent
Grauert et al.

(10) Patent No.: US 7,745,621 B2
(45) Date of Patent: Jun. 29, 2010

(54) LONG ACTING BRONCHODILATORS FOR THE TREATMENT OF RESPIRATORY DISEASES

(75) Inventors: Matthias Grauert, Biberach (DE); Thierry Bouyssou, Mietingen (DE); Philipp Lustenberger, Warthausen (DE); Steffen Breitfelder, Aβmannshardt (DE); Andreas Schnapp, Biberach (DE); Michael P. Pieper, Biberach (DE); Klaus Rudolf, Warthausen (DE); Georg Speck, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 470 days.

(21) Appl. No.: 11/125,744

(22) Filed: May 10, 2005

(65) Prior Publication Data
US 2005/0256114 A1 Nov. 17, 2005

Related U.S. Application Data

(60) Provisional application No. 60/578,490, filed on Jun. 10, 2004.

(30) Foreign Application Priority Data
May 14, 2004 (DE) .................. 10 2004 024 453

(51) Int. Cl.
*C07D 265/36* (2006.01)
*A61K 31/535* (2006.01)
*A61K 31/44* (2006.01)

(52) U.S. Cl. ............. 544/105; 514/230.5; 514/304
(58) Field of Classification Search ............. 514/230.5, 514/304; 544/105
See application file for complete search history.

(56) References Cited

U.S. PATENT DOCUMENTS

| | | | |
|---|---|---|---|
| 4,460,581 A | | 7/1984 | Schromm et al. |
| 5,223,614 A | * | 6/1993 | Schromm et al. ........... 544/105 |
| 5,362,755 A | * | 11/1994 | Barberich et al. ........... 514/649 |
| 7,244,728 B2 | | 7/2007 | Bouyssou et al. |
| 7,244,742 B2 | | 7/2007 | Pieper et al. |
| 7,417,051 B2 | | 8/2008 | Banholzer et al. |
| 2002/0022625 A1 | | 2/2002 | Walland et al. |
| 2005/0137242 A1 | | 6/2005 | Walland et al. |
| 2008/0063608 A1 | | 3/2008 | Pieper et al. |

FOREIGN PATENT DOCUMENTS

| | | |
|---|---|---|
| CA | 1 180 012 A | 12/1984 |
| CA | 2 405 745 A1 | 11/2001 |
| CA | 2 481 468 A1 | 10/2003 |
| CA | 2 495 454 A1 | 3/2004 |
| CA | 2 558 067 A1 | 10/2005 |
| DE | 102 56 317 A1 | 10/2003 |
| EP | 0 321 864 A | 6/1989 |
| EP | 1 577 306 A | 9/2005 |
| GB | 2106105 A | 4/1983 |
| WO | WO 01/83462 A | 11/2001 |
| WO | WO 02/32897 A | 4/2002 |
| WO | WO 2004/022058 A | 3/2004 |
| WO | WO 2004/045618 A | 6/2004 |

OTHER PUBLICATIONS

Milecki, J. et al: "Carbostyril Derivatives Having Potent Beta-Adrenergic Agonist Properties," Sep. 1, 1987, Journal of Medicinal Chemistry, American Chemical Society, Washington, US pp. 1563-1566.
International Search Report for PCT/EP2005/005026 mailed Sep. 28, 2005.

* cited by examiner

*Primary Examiner*—Janet L Andres
*Assistant Examiner*—John Mabry
(74) *Attorney, Agent, or Firm*—Michael P. Morris; Mary-Ellen M. Devlin; Edouard G. Lebel

(57) ABSTRACT

The invention relates to compounds of general formula 1

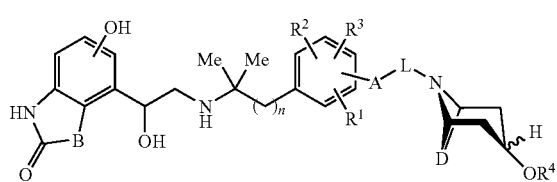

wherein n, A, B, D, L, $R^1$, $R^2$, $R^3$ and $R^4$ may have the meanings given in the claims and in the specification, processes for preparing them, and their use as pharmaceutical compositions, particularly as pharmaceutical compositions for the treatment of respiratory complaints.

12 Claims, No Drawings

LONG ACTING BRONCHODILATORS FOR THE TREATMENT OF RESPIRATORY DISEASES

This application claims priority under 35 USC 119(e) to U.S. Provisional Application 60/578,490, filed Jun. 10, 2004 and the benefit of German Application DE 10 2004 024 453, filed May 14, 2004.

The invention relates to compounds of general formula 1

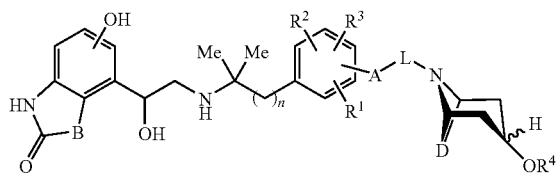

wherein n, A, B, D, L, $R^1$, $R^2$, $R^3$ and $R^4$ may have the meanings given in the claims and in the specification, processes for preparing them, and their use as pharmaceutical compositions, particularly as pharmaceutical compositions for the treatment of respiratory complaints.

DESCRIPTION OF THE INVENTION

The invention relates to compounds of general formula 1

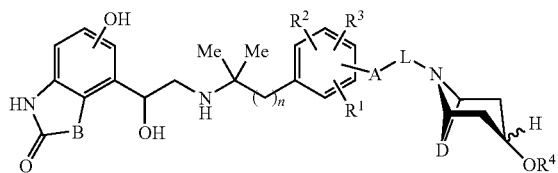

wherein n denotes 1, 2 or 3, preferably 1 and 2;

A denotes O, N or a single bond;

B denotes a double-bonded group selected from among
—$CH_2$—$CH_2$—, —CH═CH— and —$CH_2$—O—;

L denotes a double-bonded group selected from among
—CO—$(CH_2)_m$—, —CO—$(CH_2)_m$—NH—CO—$(CH_2)_o$—, —CO—$(CH_2)_m$—CO—NH—$(CH_2)_o$O—, —CO—$(CH_2)_m$—O—$(CH_2)_p$—, —$(CH_2)_p$—, —$(CH_2)_p$—O—$(CH_2)_r$—, —$(CH_2)$p—NH—CO—$(CH_2)_o$—, —$(CH_2)_p$—CO—NH—$(CH_2)_o$—, $SO_2$—$(CH_2)_m$—, —$SO_2$—$(CH_2)_m$—NH—CO—$(CH_2)_o$—, —$SO_2$—$(CH_2)_m$—CO—NH—$(CH_2)_o$—, —$SO_2$—$(CH_2)_m$—O—$(CH_2)_p$—;

m, o independently of one another denote 1 to 12;

p, r independently of one another denote 2 to 12;

$R^1$, $R^2$, $R^3$ which may be identical or different, denote hydrogen, $C_1$-$C_6$-alkyl, halogen-$C_1$-$C_6$-alkylene, OH, —$CF_3$, $CHF_2$, HO—$C_{1-6}$-alkylene, —O—$C_1$-$C_6$-alkyl, $C_6$-$C_{10}$-aryl, $C_6$-$C_{10}$-aryl-$C_1$-$C_4$-alkylene, $C_6$-$C_{10}$-aryl-$C_1$-$C_6$-alkylene-O, —COOH, —COO$C_1$-$C_6$-alkyl, —O—$C_1$-$C_6$-alkylene-COOH, —O—$C_1$-$C_6$-alkylene-COO$C_1$-$C_6$-alkyl, —$NHSO_3H$, —$NHSO_2$—$C_1$-$C_6$-alkyl, CN, $NH_2$, —NH—$C_1$-$C_6$-alkyl, —N($C_1$-$C_6$-alkyl)$_2$, $NO_2$, —S—$C_1$-$C_6$-alkyl, —$SO_2$—$C_1$-$C_6$-alkyl, —SO—$C_1$-$C_6$-alkyl, —O(CO)$C_1$-$C_6$-alkyl, —CO$C_1$-$C_6$-alkyl, —NHCO$C_1$-$C_6$-alkyl or halogen, particularly fluorine, chlorine or bromine;

D denotes a double-bonded group selected from among

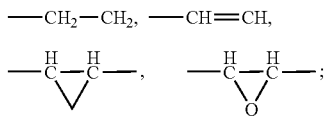

$R^4$ denotes hydrogen, $C_1$-$C_6$-alkyl, $C_6$-$C_{10}$-aryl, $C_6$-$C_{10}$-aryl-$C_1$-$C_4$-alkylene or the group

E denotes a group selected from among

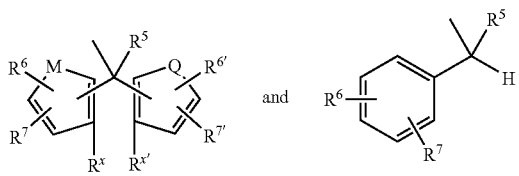

$R^5$ denotes hydrogen, hydroxy, —$C_1$-$C_4$-alkyl, —$C_1$-$C_4$-alkyloxy, —$C_1$-$C_4$-alkylene-halogen, —O—$C_1$-$C_4$-alkylene-halogen, —$C_1$-$C_4$-alkylene-OH, —$CF_3$, $CHF_2$, —$C_1$-$C_4$-alkylene-$C_1$-$C_4$-alkyloxy, —O—CO $C_1$-$C_4$-alkyl, —O—CO $C_1$-$C_4$-alkylene-halogen, —$C_1$-$C_4$-alkylene-$C_3$-$C_6$-cycloalkyl, —O—COCF$_3$ or halogen;

M and Q which may be identical or different, preferably identical, denote —O—, —S—, —NH—, $CH_2$—, —CH═CH—, or —N($C_1$-$C_4$-alkyl)-;

$R^6$, $R^7$, $R^{6'}$ and $R^{7'}$, which may be identical or different, denote hydrogen, $C_1$-$C_4$-alkyl, $C_1$-$C_4$-alkyloxy, hydroxy, —$CF_3$, —$CHF_2$, CN, $NO_2$ or halogen;

$R^x$ and $R^{x'}$ which may be identical or different denote hydrogen, $C_1$-$C_4$-alkyl, $C_1$-$C_4$-alkyloxy, hydroxy, —$CF_3$, —$CHF_2$, CN, $NO_2$ or halogen or $R^x$ and $R^{x'}$ together denote a single bond or a bridging group selected from the bridges —O—, —S—, —NH—, —$CH_2$—, —$CH_2$—$CH_2$—, —N($C_1$-$C_4$-alkyl)-, —CH($C_1$-$C_4$-alkyl)- and —C($C_1$-$C_4$-alkyl)$_2$, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Preferred are compounds of general formula 1, wherein n denotes 1 or 2;

A denotes O, N or a single bond;

B denotes a double-bonded group selected from among
—$CH_2$—$CH_2$—, —CH═CH— and —$CH_2$—O—;

L denotes a double-bonded group selected from among
—CO—$(CH_2)_m$—, —CO—$(CH_2)_m$—NH—CO—$(CH_2)_o$—, —CO—$(CH_2)_m$—CO—NH—$(CH_2)_o$—, —CO—(CH$_2$)$_m$—O—(CH$_2$)$_p$—, —(CH$_2$)$_p$—, —(CH$_2$)$_p$—O—(CH$_2$)$_r$—, —(CH$_2$)$_p$—NH—CO—(CH$_2$)$_o$—;

m, o independently of one another denote 1 to 10;

p, r independently of one another denote 2 to 10;

R$^1$, R$^2$, R$^3$ which may be identical or different, denote hydrogen, C$_1$-C$_4$-alkyl, halogen-C$_1$-C$_4$-alkylene, OH, —CF$_3$, CHF$_2$, HO—C$_{1-4}$-alkylene, —O—C$_1$-C$_4$-alkyl, C$_6$-C$_{10}$-aryl, C$_6$-C$_{10}$-aryl-C$_1$-C$_2$-alkylene, C$_6$-C$_0$-aryl-C$_1$-C$_4$-alkylene-O, —COOH, —COOC$_1$-C$_4$-alkyl, —O—C$_1$-C$_4$-alkylene-COOH, —O—C$_1$-C$_4$-alkylene-COOC$_1$-C$_4$-alkyl, —NHSO$_3$H, —NHSO$_2$—C$_1$-C$_4$-alkyl, CN, NH$_2$, —NH—C$_1$-C$_4$-alkyl, —N(C$_1$-C$_4$-alkyl)$_2$, NO$_2$, —S—C$_1$-C$_4$-alkyl, —SO$_2$—C$_1$-C$_4$-alkyl, —SO—C$_1$-C$_4$-alkyl, —O(CO)C$_1$-C$_4$-alkyl, —COC$_1$-C$_4$-alkyl, —NHCOC$_1$-C$_4$-alkyl or halogen, particularly fluorine, chlorine or bromine;

D denotes a double-bonded group selected from among

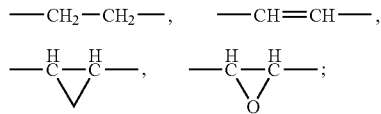

R$^4$ denotes hydrogen, C$_1$-C$_4$-alkyl, C$_6$-C$_{10}$-aryl, C$_6$-C$_{10}$-aryl-C$_1$-C$_2$-alkylene or the group

E denotes a group selected from among

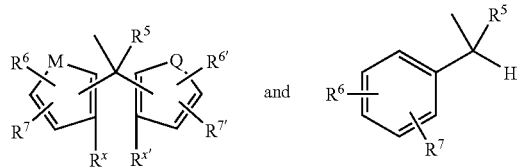

R$^5$ denotes hydrogen, hydroxy, —C$_1$-C$_4$-alkyl, —C$_1$-C$_4$-alkyloxy, —CF$_3$, —CHF$_2$, HO—CH$_2$, HO—CH$_2$—CH$_2$, fluorine, chlorine or bromine;

M and Q which may be identical or different, preferably identical, denote —O—, —S—, —NH— or —CH=CH—;

R$^6$, R$^7$, R$^{6'}$ and R$^{7'}$, which may be identical or different, denote hydrogen, C$_1$-C$_4$-alkyl, C$_1$-C$_4$-alkyloxy, hydroxy, —CF$_3$, —CHF$_2$, CN, NO$_2$, fluorine, chlorine or bromine;

R$^x$ and R$^{x'}$ which may be identical or different, denote hydrogen, C$_1$-C$_4$-alkyl, C$_1$-C$_4$-alkyloxy, hydroxy, —CF$_3$, —CHF$_2$, CN, NO$_2$, fluorine, chlorine or bromine or R$^x$ and R$^{x'}$ together denote a single bond or a bridging group selected from the bridges —O—, —S—, —NH— and —CH$_2$—, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein n denotes 1 or 2, preferably 1;

A denotes O, N or a single bond;

B denotes a double-bonded group selected from among —CH$_2$—CH$_2$—, —CH=CH— and —CH$_2$—O—;

L denotes a double-bonded group selected from among —CO—(CH$_2$)$_m$—, —CO—(CH$_2$)$_m$—NH—CO—(CH$_2$)$_o$—, —CO—(CH$_2$)$_m$—CO—NH—(CH$_2$)$_o$—, —CO—(CH$_2$)$_m$—O—(CH$_2$)$_p$—, —(CH$_2$)$_p$—, —(CH$_2$)$_p$—O—(CH$_2$)$_r$—, —(CH$_2$)$_p$—NH—CO—(CH$_2$)$_o$— m, o independently of one another denote 1 to 8;

p, r independently of one another denote 2 to 8;

R$^1$, R$^2$, R$^3$ which may be identical or different, denote hydrogen, C$_1$-C$_4$-alkyl, C$_1$-C$_4$-alkyloxy, hydroxy, —CF$_3$, —CHF$_2$, phenyl, benzyl, —COOH, —COOmethyl, —O—CH$_2$—COOH, —O—CH$_2$—COOmethyl, —O—CH$_2$—COOethyl, —O—CH$_2$—CH$_2$—COOH, —O—CH$_2$—CH$_2$—COOmethyl, —O—CH$_2$—CH$_2$—COOethyl, CN, NO$_2$, fluorine, chlorine or bromine;

D denotes a double-bonded group selected from among

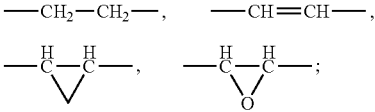

R$^4$ denotes hydrogen, methyl, ethyl, phenyl, benzyl or the group

E denotes a group selected from among

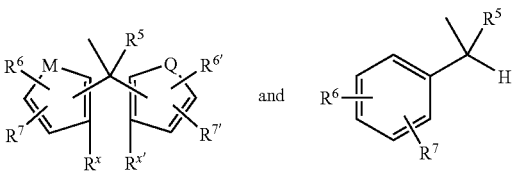

R$^5$ denotes hydrogen, hydroxy, methyl, ethyl, methyloxy, ethyloxy, —CF$_3$, HO—CH$_2$—, HO—CH$_2$—CH$_2$— or fluorine;

M and Q which may be identical or different, preferably identical, denote —S or —CH=CH—;

R$^6$, R$^7$, R$^{6'}$ and R$^{7'}$, which may be identical or different, denote hydrogen, methyl, methyloxy, —CF$_3$ or fluorine;

R$^x$ and R$^{x'}$ which may be identical or different denote hydrogen, methyl, methyloxy, —CF$_3$ or fluorine or R$^x$ and R$^{x'}$ together denote a single bond or the bridging group —O—, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein n denotes 1 and wherein A, B, D, L, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein A denotes O (oxygen) or N (nitrogen), preferably N, and wherein n, B, D, L, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein B denotes —CH=CH— or —CH$_2$—O—, preferably —CH$_2$—O— and wherein n, A, D, L, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Particularly preferred among the compounds wherein B denotes —CH$_2$—O— are the regioisomers of general formula 1a 1a wherein n, A, D, L, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein

L denotes a double-bonded group selected from among —CO—(CH$_2$)$_{1-6}$—, —CO—(CH$_2$)$_{1-6}$—NH—CO—(CH$_2$)$_{1-4}$—, —CO—(CH$_2$)$_{1-6}$—CO—NH—(CH$_2$)$_{1-4}$—, —CO—(CH$_2$)$_{1-6}$—O—(CH$_2$)$_{2-6}$—, —(CH$_2$)$_{2-6}$, —(CH$_2$)$_{2-6}$—O—(CH$_2$)$_{2-6}$—, —(CH$_2$)$_{2-6}$—NH—CO—(CH$_2$)$_{1-4}$— and wherein n, A, B, D, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein

L denotes a double-bonded group selected from among —CO—(CH$_2$)$_{1-6}$—, —CO—(CH$_2$)$_{1-4}$—NH—CO—(CH$_2$)$_{1-2}$—, —CO—(CH$_2$)$_{1-4}$—CO—NH—(CH$_2$)$_{1-2}$—, —CO—(CH$_2$)$_{1-4}$—O—(CH$_2$)$_{2-4}$—, —(CH$_2$)$_{2-4}$, —(CH$_2$)$_{2-4}$—O—(CH$_2$)$_{2-4}$—, —(CH$_2$)$_{2-4}$—NH—CO—(CH$_2$)$_{1-2}$— and wherein n, A, B, D, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein

L denotes a double-bonded group selected from among —CO—CH$_2$—NH—CO—CH$_2$—, —CO—CH$_2$—NH—CO—CH$_2$—CH$_2$—, —CO—CH$_2$—CH$_2$—NH—CO—CH$_2$—, —CO—CH$_2$—CH$_2$—NH—CO—CH$_2$—CH$_2$, —CO—CH$_2$—CH$_2$—CH$_2$—NH—CO—CH$_2$—, —CO—CH$_2$—CH$_2$—CH$_2$—NH—CO—CH$_2$—CH$_2$—, —CO—CH$_2$—CH$_2$—CH$_2$—CH$_2$—NH—CO—CH$_2$—, —CO—CH$_2$—CH$_2$—CH$_2$—CH$_2$—NH—CO—CH$_2$—CH$_2$—, —CO—CH$_2$—CH$_2$—, —CO—CH$_2$—CH$_2$—CH$_2$—, —CO—CH$_2$—CH$_2$—CH$_2$—CH$_2$—, —CO—CH$_2$—CH$_2$—CH$_2$—CH$_2$—CH$_2$—, —CO—CH$_2$—CH$_2$—CH$_2$—CH$_2$—CH$_2$—CH$_2$—, —CO—CH$_2$—CH$_2$—CH$_2$—CH$_2$—CH$_2$—CH$_2$—CO—CH$_2$—CO—NH—CH$_2$—, —CO—CH$_2$—CO—NH—CH$_2$—CH$_2$—, —CO—CH$_2$—CH$_2$—CO—NH—CH$_2$—, —CO—CH$_2$—CH$_2$—CO—NH—CH$_2$—CH$_2$—, —CO—CH$_2$—CH$_2$—CH$_2$—CO—NH—CH$_2$—, —CO—CH$_2$—CH$_2$—CH$_2$—CO—NH—CH$_2$—CH$_2$—, —CO—CH$_2$—CH$_2$—CH$_2$—CH$_2$—CO—NH—CH$_2$— and —CO—CH$_2$—CH$_2$—CH$_2$—CH$_2$—CO—NH—CH$_2$—CH$_2$— and wherein n, A, B, D, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein

L denotes a double-bonded group selected from among —CO—CH$_2$—CH$_2$—NH—CO—CH$_2$—, —CO—CH$_2$—CH$_2$—NH—CO—CH$_2$—CH$_2$—, —CO—CH$_2$—CH$_2$—CH$_2$—NH—CO—CH$_2$—, —CO—CH$_2$—CH$_2$—CH$_2$—NH—CO—CH$_2$—CH$_2$—, —CO—CH$_2$—CH$_2$—NH—CO—CH$_2$—CH$_2$—, —CO—CH$_2$—CH$_2$—CH$_2$—NH—CO—CH$_2$— and —CO—CH$_2$—CH$_2$—CH$_2$—NH—CO—CH$_2$—CH$_2$— and wherein n, A, B, D, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein $R^1, R^2, R^3$ which may be identical or different, denote hydrogen, methyl, ethyl, methoxy, ethoxy, OH, —$CF_3$, —$CHF_2$, fluorine, chlorine or bromine, preferably hydrogen, methyl, methoxy, —$CF_3$, —$CHF_2$ or fluorine, particularly preferably hydrogen, methyl, or fluorine, and wherein n, A, B, D, L and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein

D denotes a double-bonded group selected from among

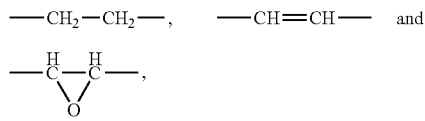

preferably

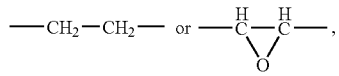

particularly preferably —$CH_2$—$CH_2$— and wherein n, A, B, L, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein

D denotes a double-bonded group selected from among

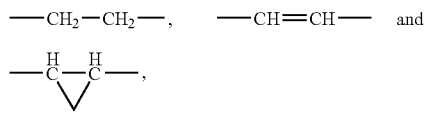

preferably

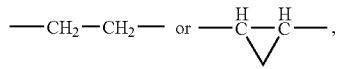

particularly preferably

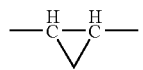

and wherein n, A, B, L, $R^1$, $R^2$, $R^3$ and $R^4$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein $R^4$ denotes hydrogen, methyl, ethyl, phenyl or benzyl, preferably, hydrogen, methyl or benzyl, particularly preferably hydrogen and wherein n, A, B, D, L, $R^1$, $R^2$ and $R^3$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein $R^4$ denotes the group

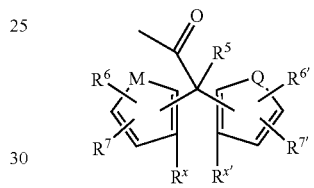

wherein $R^5$ denotes hydrogen, hydroxy, methyl or fluorine, preferably, hydrogen, hydroxy or methyl, particularly preferably hydroxy;

M and Q which may be identical or different, preferably identical, denote —S— or —CH=CH—;

$R^6$, $R^7$, $R^{6'}$ and $R^{7'}$, which may be identical or different, denote hydrogen, —$CF_3$ or fluorine, preferably hydrogen;

$R^x$ and $R^{x'}$ which may be identical or different denote hydrogen, —$CF_3$ or fluorine, preferably hydrogen or $R^x$ and $R^{x'}$ together denote a single bond or the bridging group —O— and wherein n, A, B, D, L, $R^1$, $R^2$ and $R^3$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Also preferred are compounds of general formula 1, wherein $R^4$ denotes the group

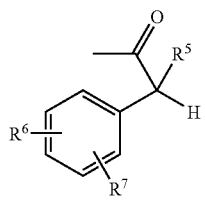

wherein $R^5$ denotes hydrogen, hydroxy, methyl, —$CF_3$ or HO—$CH_2$—;

$R^6$ and $R^7$ which may be identical or different, denote hydrogen, methyl, methyloxy, —$CF_3$ or fluorine, preferably hydrogen or fluorine, particularly preferably hydrogen;

and wherein n, A, B, D, L, $R^1$, $R^2$ and $R^3$ may have the meanings given above and hereinafter, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

In another aspect the present invention relates to the above-mentioned new compounds of formula 1 in the form of the individual optical isomers, mixtures of the individual enantiomers or optionally diastereomers or racemates. Particularly preferred are compounds of formula 1 in the form of the enantiomers or diastereomerically pure compounds, while exceptional importance attaches to the R-enantiomers or optionally diastereomers of the compounds of formula 1 according to the invention which may be represented by general formula R-1,

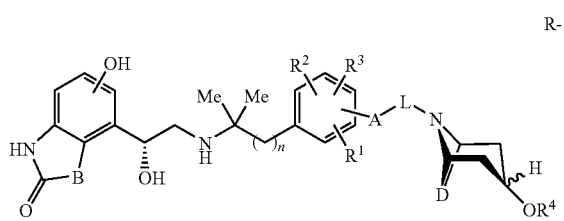

R-1 wherein n, A, B, D, L, $R^1$, $R^2$, $R^3$ and $R^4$ may have the meanings given above, optionally in the form of the acid addition salts thereof with pharmacologically acceptable acids as well as optionally in the form of the solvates and/or hydrates thereof.

The compounds of general formula 1 may occur in 3 different regioisomers with regard to the position of the hydroxyl function.

Preferred regioisomers of the compounds of general formula 1 according to the invention are those of general formula Regio-1a

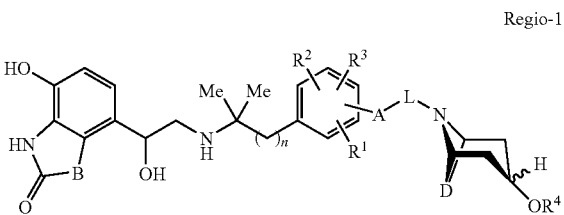

Regio-1a wherein n, A, B, D, L, $R^1$, $R^2$, $R^3$ and $R^4$ may have the meanings given above, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Other preferred regioisomers of the compounds of general formula 1 according to the invention are those of general formula Regio-1b

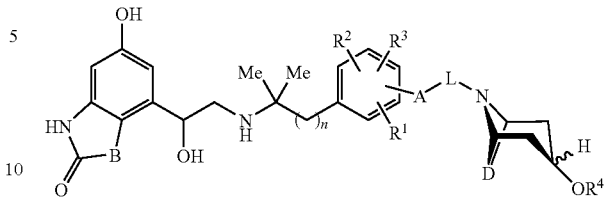

Regio-1b wherein n, A, B, D, L, $R^1$, $R^2$, $R^3$ and $R^4$ may have the meanings given above, optionally in the form of the individual enantiomers or optionally diastereomers, mixtures of the individual enantiomers or optionally diastereomers or racemates, optionally in the form of the acid addition salts thereof with pharmacologically acceptable acids as well as optionally in the form of the solvates and/or hydrates thereof.

Unless otherwise stated, the alkyl groups are straight-chained or branched alkyl groups having 1 to 6, preferably 1 to 4 carbon atoms. The following are mentioned by way of example: methyl, ethyl, propyl or butyl. In some cases the abbreviations Me, Et, Prop or Bu are used to denote the groups methyl, ethyl, propyl or butyl. Unless otherwise stated, the definitions propyl and butyl include all the possible isomeric forms of the groups in question. Thus, for example, propyl includes n-propyl and iso-propyl, butyl includes iso-butyl, sec.butyl and tert.-butyl, etc.

Unless otherwise stated, the alkylene groups are branched and unbranched double-bonded alkyl bridges with 1 to 6, preferably 1 to 4 carbon atoms. Examples include: methylene, ethylene, propylene or butylene.

Unless otherwise stated, the alkylene-halogen groups are branched and unbranched double-bonded alkyl bridges having 1 to 6, preferably 1 to 4 carbon atoms which are mono-, di- or trisubstituted, preferably disubstituted, by a halogen. Accordingly, unless otherwise stated, the alkylene-OH groups are branched and unbranched double-bonded alkyl bridges having 1 to 6, preferably 1 to 4 carbon atoms which are mono-, di- or trisubstituted, preferably monosubstituted, by a hydroxy.

Unless otherwise stated, the term alkyloxy groups (or —O-alkyl groups or alkoxy groups) denotes branched and unbranched alkyl groups having 1 to 6, preferably 1 to 4 carbon atoms which are linked via an oxygen atom. Examples of these include: methyloxy, ethyloxy, propyloxy or butyloxy. The abbreviations MeO—, EtO—, PropO— or BuO— are used in some cases to denote the groups methyloxy, ethyloxy, propyloxy or butyloxy. Unless otherwise stated, the definitions propyloxy and butyloxy include all possible isomeric forms of the groups in question. Thus, for example, propyloxy includes n-propyloxy and iso-propyloxy, butyloxy includes iso-butyloxy, sec.butyloxy and tert.-butyloxy, etc. In some cases, within the scope of the present invention, the term alkoxy is used instead of the term alkyloxy. Accordingly, the terms methoxy, ethoxy, propoxy or butoxy may also be used to denote the groups methyloxy, ethyloxy, propyloxy or butyloxy.

The term $C_6$-$C_{10}$-aryl denotes an aromatic ring system with 6 to 10 carbon atoms. Preferred aryl groups are phenyl or naphthyl.

The term $C_6$-$C_{10}$-aryl-$C_1$-$C_4$-alkylene denotes an aromatic ring system with 6 to 10 carbon atoms which is linked via an alkylene bridge with 1 to 4 C atoms. Preferred aralkylene groups are benzyl and phenylethyl.

Within the scope of the present invention halogen denotes fluorine, chlorine, bromine or iodine. Unless otherwise stated, fluorine, chlorine and bromine are the preferred halogens.

In another aspect the present invention relates to the above-mentioned compounds of formula 1 in the form of the acid addition salts thereof with pharmacologically acceptable acids as well as optionally in the form of the solvates and/or hydrates thereof.

By acid addition salts with pharmacologically acceptable acids are meant for example salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

Of the above-mentioned acid addition salts the salts of hydrochloric acid, methanesulphonic acid, benzoic acid and acetic acid are particularly preferred according to the invention.

The compounds according to the invention of formula 1 are characterised by their antagonistic activity at muscarinic receptors of subtype M3 and by their agonistic activity at the adrenergic β2-receptor. The compounds according to the invention have Ki values of less than 1 μM with regard to the affinity for the M3-receptor and EC50 values of less than 1 μM with regard to the β2-agonistic activity. These values were determined using the procedure described below.

M3-Receptor Binding:

Membrane preparations from CHO cells (Chinese hamster ovary) transfected with the corresponding gene of the human muscarinic receptor subtype hm3 were used for the binding assay. The test was carried out in a final volume of 1 ml and consisted of 100 μl of unlabelled substance in various concentrations, 100 μl radioligand (3H—N-methylscopolamine 2 nmol/L (3H-NMS), 200 μl membrane preparation and 600 μl HEPES buffer (20 mmol/L HEPES, 10 mmol/L $MgCl_2$, 100 mmol/L NaCl, adjusted to pH 7.4 with 1 mol/L NaOH). The non-specific binding was determined with 10 μmol/L atropine.

The preparation was incubated for 45 min. at 37° C. in 96-well microtitre plates (Beckman, polystyrene, No. 267001) as a double measurement. The incubation was ended by filtering using an Inotech Cell Harvester (type IH 110) through Whatman G-7 filters. The filters were washed with 3 ml of ice-cooled HEPES buffer and dried before the measurement. The radioactivity of the filter mats was measured simultaneously by two-dimensional digital Autoradiograph (Berthold, Wildbad, type 3052). The Ki values were calculated using implicit equations derived directly from the mass-action law, with the model for the 1 receptor 2 ligand reaction (SysFit software, SCHITTKOWSKI).

LITERATURE

BONNER T I, New subtypes of muscarinic acetylcholine receptors Trends Pharmacol. Sci. 10, Suppl.: 11-15 (1989);
SCHITTKOWSKI K: Parameter estimation in systems of nonlinear equations Numer Math. 68: 129-142 (1994).

β2-Agonistic Activity:

The agonistic activity at the $β_2$ receptor was determined by measuring cAMP synthesis in CHO (Chinese hamster ovary) cells which stably expressed the human $β_2$ adrenergic receptor.

After growing to 70-80% confluence the cells were washed 3× with PBS, removed from the plate and suspended in stimulating buffer (0.1% BSA, 0.5 mM IBMX, 5 mM Hepes, 1×HBSS) with a cell count of 0.65×10 cells/ml. Then 20 μl of the cell suspension were incubated with 10 μl test substance (in 0.9% NaCl, 3% DMSO) (final concentration of the test substance from 0.01 nM to 10 μM). After incubation for 30 min at ambient temperature the cells were lysed by the addition of 20 μl lysing buffer (0.3% Tween 20, 5 mM Hepes, 0.1% BSA) for at least 30 min on ice. Then 5 μl of the lysed material were pipetted in a four-fold measurement into a 384 well plate (OptiPlate; Packard Bioscience). The synthesised cAMP was detected using the AlphaScreen cAMP Detection Kit made by BioSignal Packard and subsequently measured on a Fusion Reader (Packard Bioscience).

The resulting Alpha Screen Counts (ACS) were converted directly into cAMP synthesis using a cAMP standard curve. To determine the stimulation level ("intrinsic activity") on each test plate cells were combined with only the control solution (0.9% NaCl, 3% DMSO) (=non-stimulated cells, "low") or with the complete 13 receptor agonist isoprenalin (1 nM to 10 μM; =to 100% stimulated cells; "high"). To analyse the data the maximum cAMP synthesis of the test substance in question was calculated with that of the complete 13 agonist isoprenalin according to the following formula: [cAMP (substance)]−[cAMP(low)]×100/[cAMP(high)−[cAMP (low)].

The ED50 was calculated with the Software Graph Pad Prism.

The compounds according to the invention of formula 1 are characterised by their versatility of use in the therapeutic field. Particular mention should be made according to the invention of those possible applications for which the compounds according to the invention of formula 1 are preferably used on account of their pharmaceutical efficacy as anticholinergics and betamimetics.

In another aspect the present invention therefore relates to the above-mentioned new compounds of formula 1 as pharmaceutical compositions. The present invention also relates to the use of the above-mentioned compounds of general formula 1 for preparing a pharmaceutical composition for the treatment of respiratory complaints.

The present invention preferably relates to the use of the above-mentioned compounds of general formula 1 for preparing a pharmaceutical composition for the treatment of respiratory complaints, which are selected from among obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary oedema.

It is preferable to use compounds of general formula 1 for preparing a pharmaceutical composition for the treatment of obstructive pulmonary diseases which are selected from among COPD (chronic obstructive pulmonary disease), bronchial asthma, paediatric asthma, severe asthma, acute asthma attacks and chronic bronchitis, while it is particularly preferable according to the invention to use them for preparing a pharmaceutical composition for the treatment of bronchial asthma.

It is also preferable to use compounds of general formula 1 for preparing a pharmaceutical composition for the treatment of pulmonary emphysemas that have their origin in COPD (chronic obstructive pulmonary disease) or α1-proteinase inhibitor deficiency.

It is also preferable to use compounds of general formula 1 for preparing a pharmaceutical composition for the treatment of restrictive pulmonary diseases, which are selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

It is also preferable to use compounds of general formula 1 for preparing a pharmaceutical composition for the treatment of interstitial pulmonary diseases which are selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

It is also preferable to use compounds of general formula 1 for preparing a pharmaceutical composition for the treatment of cystic fibrosis or mucoviscidosis.

It is also preferable to use compounds of general formula 1 for preparing a pharmaceutical composition for the treatment of bronchitis, such as for example bronchitis caused by bacterial or viral infection, allergic bronchitis and toxic bronchitis.

It is also preferable to use compounds of general formula 1 for preparing a pharmaceutical composition for the treatment of bronchiectasis.

It is also preferable to use compounds of general formula 1 for preparing a pharmaceutical composition for the treatment of ARDS (adult respiratory distress syndrome).

It is also preferable to use compounds of general formula 1 for preparing a pharmaceutical composition for the treatment of pulmonary oedemas, for example toxic pulmonary oedema after aspiration or inhalation of toxic substances and foreign substances.

Particularly preferably, the present invention relates to the use of the compounds of formula 1 for preparing a pharmaceutical composition for the treatment of asthma or COPD. Also of particular importance is the above-mentioned use of compounds of formula 1 for preparing a pharmaceutical composition for once-a-day treatment of inflammatory and obstructive respiratory complaints, particularly for the once-a-day treatment of asthma or COPD.

Moreover the present invention relates to a method of treating the above-mentioned diseases, characterised in that one or more of the above-mentioned compounds of general formula 1 are administered in therapeutically effective amounts. The present invention preferably relates to methods of treating asthma or COPD, characterised in that one or more of the above-mentioned compounds of general formula 1 are administered once a day in therapeutically effective amounts.

The compounds according to the invention of formula 1 are characterised by their long-lasting effect when administered by inhalation. This has been demonstrated by the following trial:

In the anaesthetised dog bronchoconstriction can be induced by the intravenous administration of acetylcholine (ACh). Inhaled bronchodilators, for example anticholinergics or beta-2-mimetics, protect the animals from this ACh-induced bronchospasm. In the study, in beagles anaesthetised with propofol and artificially ventilated, a vein, e.g. the cephalic artery, was prepared for the intravenous administration of ACh. During the anaesthesia the animals' vital signs are measured continuously and the physiological body temperature is kept constant by means of heating systems. The transpulmonary pressure was measured using a differential pressure gauge. A Fleisch pneumotachometer is connected to the trachea to measure the breathing rate. ECG and diastolic/systolic blood pressure are also measured. After a period of acclimatisation the test substances are given to the animals by inhalation from a Respimat. ACh is administered 30 and 15 min before, and 5, 10, 20, 30, 120 and 180 min after the inhalation of the text substance. After the last measurement the anaesthetic drip is removed and the animals regain consciousness. The next day the animals are briefly anaesthetised again in order to measure the bronchoprotection 24 h after the administration of the substance. The data obtained are calculated as % bronchoprotection compared with the values before the substance was administered.

The compounds of general formula 1 may be obtained by the method shown in Diagram 1.

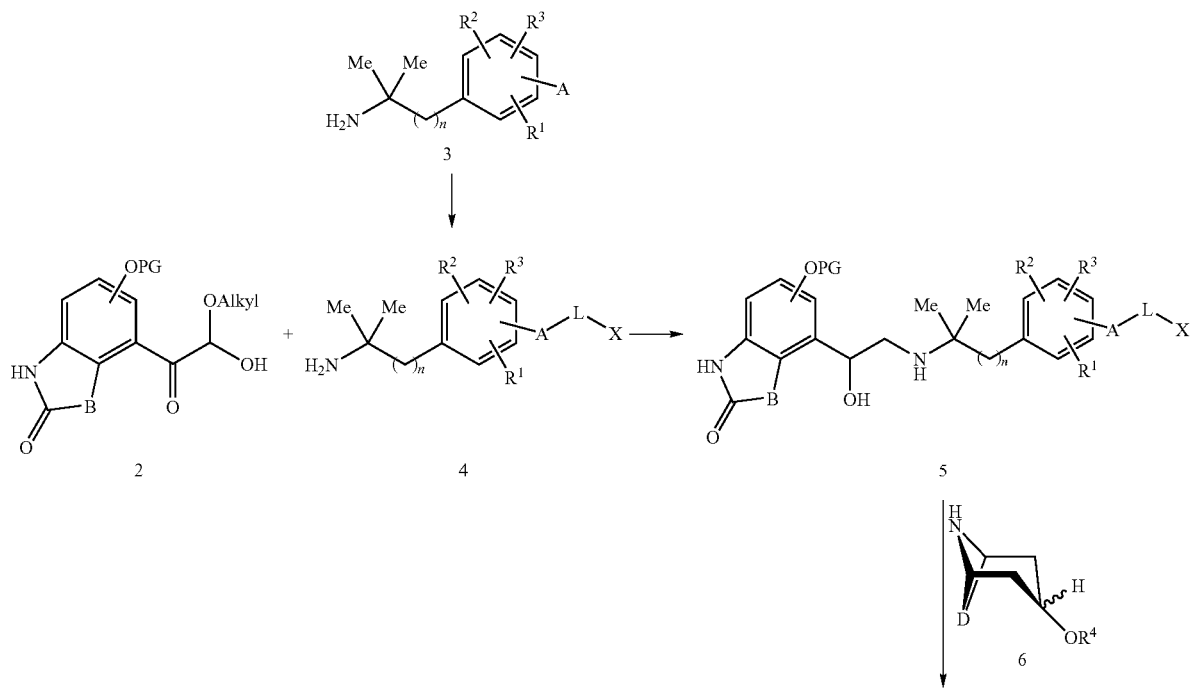

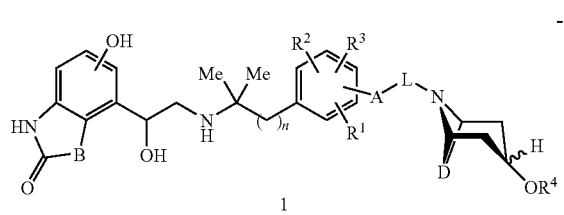

-continued

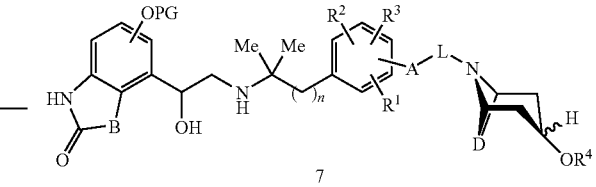

In the starting compounds and intermediate products shown in Diagram 1 the groups n, A, B, D, L, $R^1$, $R^2$, $R^3$ and $R^4$ may be defined as hereinbefore and the groups OPG and X may be defined as below.

A compound of general formula 2 is condensed with a compound of general formula 4 in a solvent, preferably an alcohol, particularly preferably ethanol, to form the Schiff base and then reduced with a reducing agent such as e.g. $H_2/Pd/C$ or $NaBH_4$ to form the aminoalcohol 5. If X is a protected amino group, in the next step the protective group, preferably the BOC group, is cleaved with trifluoroacetic acid and acylated with an ω-halocarboxylic acid halide. Then it is substituted with compound 6 and compound 7 is obtained. After the cleaving of the protective group PG, by hydrogenolytic cleaving in the case of a benzyl protective group, the target compound 1 is obtained.

If X in compound 5 is a leaving group, this may be substituted directly with compound 6.

Depending on the nature of A and L the compound 4 may be prepared by amide formation, ester formation, amine formation or ether formation from compound 3 and a suitable linker L using methods known per se.

In another aspect the present invention relates to the intermediate products of general formula 4

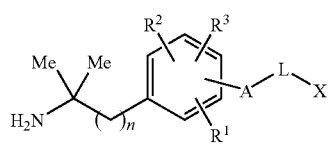

wherein

X denotes chlorine, bromine, iodine, methanesulphonate, trifluoromethanesulphonate, p-toluenesulphonate, or an amino function protected by a suitable protective group, preferably —NH—Boc, —NH-Cbz, —NH-Fmoc, —NH-Teoc, or —NH-Alloc and wherein n, A, L, $R^1$, $R^2$ and $R^3$ may have the above-mentioned meanings.

In accordance with the nomenclature used in the art, —NH—Boc denotes tert-butylcarbamate, —NH-Cbz denotes benzylcarbamate, —NH-Fmoc denotes 9-fluorenylmethylcarbamate, —NH-Teoc denotes 2-trimethylsilylethylcarbamate, and —NH-Alloc denotes allylcarbamate.

Preferred are intermediate products of general formula 4, wherein

X denotes chlorine, bromine, iodine, methanesulphonate, trifluoromethanesulphonate, p-toluenesulphonate or —NH—Boc and wherein n, A, L, $R^1$, $R^2$ and $R^3$ may have the meanings given above.

In another aspect the present invention relates to the intermediate products of general formula 5

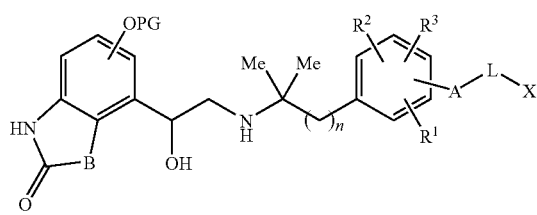

wherein

OPG denotes a hydroxy function protected by a protective group PG, preferably —O—$C_1$-$C_4$-alkyl, —O-benzyl or —O—$CH_2$—O—$C_1$-$C_4$-alkyl, preferably —O-methyl, —O-ethyl, —O-benzyl or —O—$CH_2$—O-methyl, particularly preferably —O-ethyl or —O-benzyl, particularly preferably —O-benzyl and wherein n, A, L, X, $R^1$, $R^2$ and $R^3$ may have the meanings given above.

In another aspect the present invention relates to the intermediate products of general formula 7

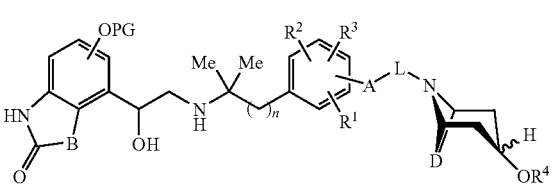

wherein n, A, L, D, X, OPG, $R^1$, $R^2$ and $R^3$ may have the meanings given above.

The new compounds of general formula 1 may be prepared analogously to the following Examples. The Examples described below are intended to illustrate the invention without however restricting it.

Example 1

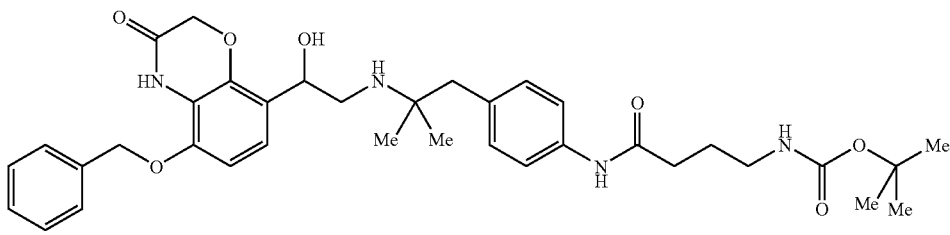

17.00 g (203 mmol) 4-tert-butoxycarbonylamino-butyric acid in 300 mL THF is cooled to −25° C., combined with 9.7 mL (101 mmol) N-methylmorpholine and 11.4 mL (137 mmol) isobutyl chloroformate and stirred for 30 min at −25° C. 17.5 g (201 mmol) 4-(2-amino-2-methyl-propyl)-phenylamine and 9.7 mL (101 mmol) N-methylmorpholine are added, the mixture is slowly heated to RT and stirred for 16 h at RT. The reaction mixture is combined with sat. aqueous sodium bicarbonate solution, the phases are separated and the aqueous phase is extracted with EtOAc. The combined org. extracts are dried over sodium sulphate and evaporated down i. vac. The residue is purified through silica gel (eluant: $CH_2Cl_2$/MeOH/$NH_4OH$ gradient from 95/4.5/0.5 to 60/35/5). The corresponding fractions are combined and evaporated down i. vac. Yield 21.5 g (74%) as a brown oil.

40 g (112 mmol) 5-benzyloxy-8-(2-ethoxy-2-hydroxyacetyl)-4H-benzo[1,4]oxazin-3-one and 40 g (114 mmol) N-(2-amino-2-methyl-proyl)-phenyl)-4-(tert-butyloxy-carbonylamino)-butanoic acid amide are placed in 300 mL ethanol and heated to 80° C. for 30 min, then stirred for 30 min at 50° C. Then the mixture is cooled, $NaBH_4$ is added and the resulting mixture is stirred for 2 h at RT. It is combined with some acetone, stirred for 30 min at RT, acidified with glacial acetic acid and evaporated down i. vac. The residue is taken up in dichloromethane, washed with 1 M $KHSO_4$ solution and then with 15% $K_2CO_3$ solution. The org. phase is again extracted with sat. $NaHCO_3$ solution, dried over $Na_2SO_4$ and evaporated down i. vac. The residue is purified through silica gel (eluant: $CH_2Cl_2$/MeOH/$NH_4OH$ gradient from 95/4.5/0.5 to 60/35/5). Corresponding fractions are combined and evaporated down i. vac. Yield 60.5 g (84%) oil.

Example 2

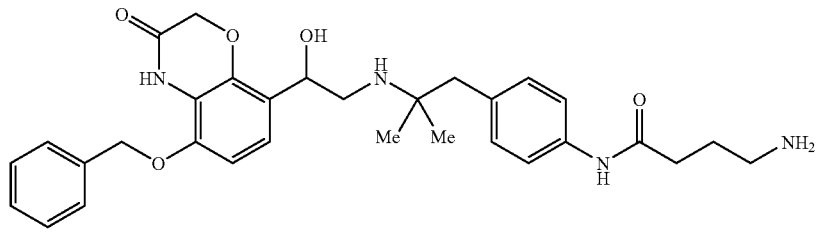

57 g (89 mmol) of the compound of Example 1 are dissolved in 800 mL dichloromethane, 100 mL trifluoroacetic acid are added and the mixture is stirred overnight at RT. The solvent is eliminated i. vac., the residue is taken up in ethyl acetate and water, made alkaline with 130 mL 30% NaOH and the phases are separated. The aqueous phase is again extracted with ethyl acetate, the org. extracts are combined and washed with sat. $NaHCO_3$ solution, dried over $Na_2SO_4$ and evaporated down i. vac. The residue is purified through silica gel (eluant: $CH_2Cl_2$/MeOH/$NH_4OH$=90/10/1). The corresponding fractions are combined and evaporated down i. vac. Yield: 20.5 g (42%) brown solid.

Example 3

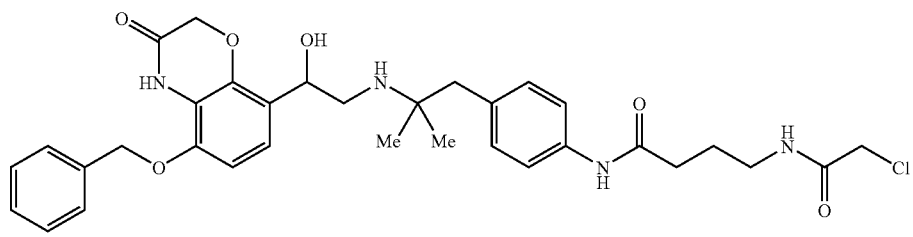

2 g (3.7 mmol) of the compound from Example 2 are dissolved in 10 mL dichloromethane, 0.65 mL (3.7 mmol) Hünig base are added and the mixture is cooled in the ice bath. 0.3 mL (3.7 mmol) chloroacetylchoride are dissolved in 10 mL dichloromethane and slowly added dropwise. The mixture is stirred for 30 min with cooling, then the ice bath is removed and the mixture is stirred for 2 h at RT. The reaction mixture is diluted with dichloromethane and washed with 15% $K_2CO_3$ solution. The org. phase is dried over $Na_2SO_4$ and evaporated down i. vac. The residue is purified through silica gel (eluant: $CH_2Cl_2$/MeOH/$NH_4OH$ gradient from 95/4.5/0.5 to 60/35/5). The corresponding fractions are combined and evaporated down i. vac. Yield: 2.1 g (92%) oil.

Example 4

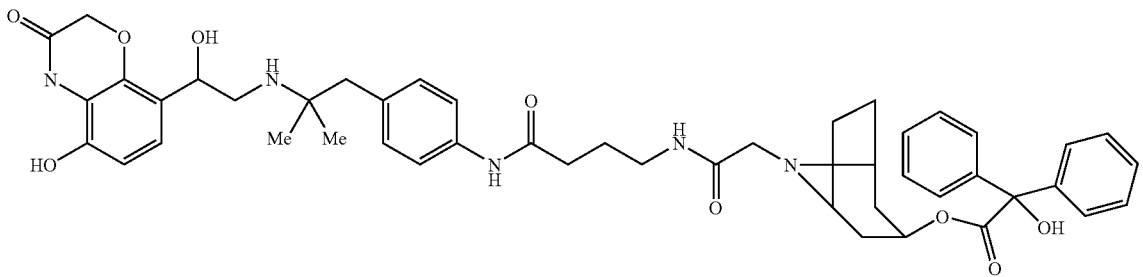

470 mg (0.7 mmol) of the compound from Example 3 are dissolved in 10 mL D F, 300 mg (0.8 mmol) nortropanyl benzylate and 370 mg $K_2CO_3$ are added and the mixture is stirred overnight at 100° C. The solvent is eliminated i. vac., the residue is taken up in water and extracted twice with ethyl acetate. The org. extracts are combined, dried over $Na_2SO_4$ and evaporated down i. vac. The residue is purified through silica gel (eluant: $CH_2Cl_2$/MeOH/$NH_4OH$ gradient from 95/4.5/0.5 to 60/35/5). The corresponding fractions are combined and evaporated down i. vac. The residue is triturated in diisopropylether and suction filtered. Then it is dissolved in 20 mL methanol, and shaken on 50 mg Pd/C (10%) and 3 bar hydrogen for 2 h at RT. The cat. is suction filtered, the solvent is evaporated down i. vac., the residue is triturated in diisopropylether and suction filtered. Yield: 102 mg (16%); mass spectroscopy: [M+H]=834.

Example 5

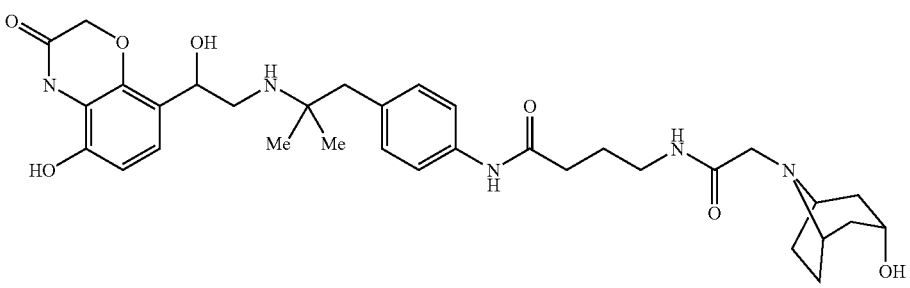

100 mg (0.16 mmol) of the compound from Example 3 are dissolved in THF, 25 mg (0.20 mmol) nortropanol and 0.035 mL (0.20 mmol) Hünig base are added. The mixture is stirred for 72 h at 60° C., the solvent is eliminated i. vac., the residue is taken up in dichloromethane and washed with sat. $NaHCO_3$ solution. The org. phase is dried over $Na_2SO_4$ and evaporated down i. vac. The residue is purified through silica gel (eluant: $CH_2Cl_2$/MeOH/$NH_4OH$ gradient from 9514.5/0.5 to 60/35/5). The corresponding fractions are combined and evaporated down i. vac. The residue is triturated in diisopropylether and suction filtered. Then it is dissolved in 10 mL methanol and shaken on 40 mg Pd/C (10%) and 3 bar hydrogen for 2 h at RT. The cat. is suction filtered, the solvent is evaporated down i. vac., the residue is triturated in diisopropylether and suction filtered. Yield: 64 mg (64%); mass spectroscopy: [M+H]=624.

Example 6

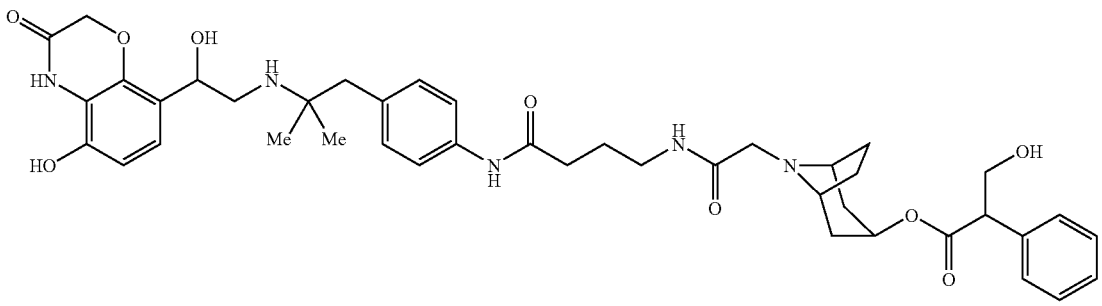

470 mg (0.75 mmol) of the compound of Example 3 are dissolved in 100 mL DMF, 210 mg (0.76 mmol) nortropanyl tropanoaate and 370 mg $K_2CO_3$ are added and the mixture is stirred overnight at RT. The solvent is eliminated i. vac., the residue is taken up in 15% $K_2CO_3$ solution and extracted twice with dichloromethane. The org. extracts are combined, dried over $Na_2SO_4$ and evaporated down i. vac. The residue is purified through silica gel (eluant: $CH_2Cl_2$/MeOH/$NH_4OH$ gradient from 95/4.5/0.5 to 60/35/5). The corresponding fractions are combined, evaporated down i. vac., the residue is triturated in diisopropylether and suction filtered. Then it is dissolved in 15 mL methanol and shaken on 50 mg Pd/C (10%) and 3 bar hydrogen for 1 h at RT. The cat. is suction filtered, the solvent is evaporated down i. vac., the residue is triturated in diisopropylether and suction filtered. Yield: 85 mg (16%); mass spectroscopy: [M+H]=772.

Suitable preparations for administering the compounds of formula 1 include tablets, capsules, suppositories, solutions, powders, etc. The proportion of pharmaceutically active compound or compounds should be in the range from 0.05 to 90% by weight, preferably 0.1 to 50% by weight of the total composition. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, arabic gum, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations of active substances according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

When the compounds of formula 1 are used, as preferred according to the invention, for the treatment of respiratory complaints, it is particularly preferable to use preparations or pharmaceutical formulations that can be administered by inhalation. Suitable formulations for inhalation include inhalable powders, propellant-driven metered—dose aerosols or propellant-free inhalable solutions. Within the scope of the present invention the term propellant-free inhalable solutions also includes concentrates or sterile ready-to-use inhalable solutions. The formulations which may be used within the scope of the present invention are described in detail in the next part of the specification.

The inhalable powders which may be used according to the invention may contain 1 either on their own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. In some cases it may seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect.

The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the µg range. The dosage may then be in the gram range, for example.

In another aspect the present invention relates to the above-mentioned pharmaceutical formulations, characterised in that they contain a compound of formula 1, as such, particularly preferably the above-mentioned pharmaceutical formulations for use by inhalation.

The following formulation examples illustrate the present invention without restricting its scope:

| A) Ampoule solution | |
| --- | --- |
| active substance of formula 1 | 25 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| B) Metered-dose aerosol (suspension) | |
| --- | --- |
| active substance of formula 1 | 0.03 wt. % |
| sorbitolan trioleate | 0.6 wt. % |
| TG134A:TG227 2:1 | 99.37 wt. % |

The suspension is poured into a conventional aerosol container with metering valve. Preferably 50 μl suspension are delivered in each puff. The active substance may if desired also be delivered in higher doses.

| C) Metered-dose aerosol (solution) | |
| --- | --- |
| active substance of formula 1 | 0.03 wt. % |
| ethanol abs. | 20 wt. % |
| aqueous HCl 0.01 mol/l | 2.0 wt. % |
| TG134A | 77.97 wt. % |

The solution is prepared in the conventional manner by mixing the individual constituents:

| D) Inhalable powder | |
| --- | --- |
| active substance of formula 1 | 80 μg |
| lactose monohydrate | ad 10 mg |

The inhalable powder is prepared in the conventional manner by mixing the individual constituents.

The invention claimed is:

1. A compound of formula 1 wherein
n denotes 1 or 2;
A denotes O, N or a single bond;
B denotes —$CH_2$—O—;
L denotes a double-bonded group selected from among
—CO—$(CH_2)_m$—, —CO—$(CH_2)_m$—NH—CO—$(CH_2)_o$—, —CO—$(CH_2)_m$—CO—NH—$(CH_2)_o$—, —CO—$(CH_2)_m$—O—$(CH_2)_p$—, —$(CH_2)_p$—, —$(CH_2)_p$—O—$(CH_2)_r$—, —$(CH_2)_2$—NH—CO—$(CH_2)_o$—
m, o independently of one another denote 1 to 8;
p, r independently of one another denote 2 to 8;
$R^1$, $R^2$, $R^3$ which may be identical or different, denote hydrogen, $C_1$-$C_4$-alkyl, $C_1$-$C_4$-alkyloxy, hydroxy, —$CF_3$, —$CHF_2$, phenyl, benzyl, —COOH, —COOmethyl, —O—$CH_2$—COOH, —O—$CH_2$—COOmethyl, —O—$CH_2$—COOethyl, —O—$CH_2$—$CH_2$—COOH, —O—$CH_2$—$CH_2$—COOmethyl, —O—$CH_2$—$CH_2$—COOethyl, CN, $NO_2$, fluorine, chlorine or bromine;
D denotes a double-bonded group selected from among —$CH_2$—$CH_2$— and —CH=CH—;
$R^4$ denotes hydrogen, methyl, ethyl, phenyl, benzyl or the group E denotes a group selected from among $R^5$ denotes hydrogen, hydroxy, methyl, ethyl, methyloxy, ethyloxy, —$CF_3$, HO—$CH_2$, HO—$CH_2$—$CH_2$ or fluorine;
M and Q which may be identical or different, preferably identical, denote —S or —CH=CH—;
$R^6$, $R^7$, $R^{6'}$ and $R^{7'}$, which may be identical or different, denote hydrogen, methyl, methyloxy, —$CF_3$ or fluorine;
$R^x$ and $R^{x'}$ which may be identical or different denote hydrogen, methyl, methyloxy, —$CF_3$ or fluorine
or
$R^x$ and $R^{x'}$ together denote a single bond or the bridging group —O—, optionally in the form of the individual enantiomers or optionally diastereomers, mixtures of the individual enantiomers or optionally diastereomers or racemates, optionally in the form of the acid addition salts thereof with pharmacologically acceptable acids.

2. The compound of formula 1 according to claim 1, wherein n denotes 1, optionally in the form of the individual enantiomers or optionally diastereomers, mixtures of the individual enantiomers or optionally diastereomers or racemates, optionally in the form of the acid addition salts thereof with pharmacologically acceptable acids.

3. The compound of formula 1 according to claim 1, wherein A denotes O (oxygen) or N (nitrogen), optionally in the form of the individual enantiomers or optionally diaste- 4. The compound of formula 1 according to claim 1, wherein B denotes —CH$_2$—O—, optionally in the form of the individual enantiomers or optionally diastereomers, mixtures of the individual enantiomers or optionally diastereomers or racemates, optionally in the form of the acid addition salts thereof with pharmacologically acceptable acids.

5. The compound of formula 1 according to claim 1, wherein

L denotes a double-bonded group selected from among —CO—(CH$_2$)$_{1-6}$—, —CO—(CH$_2$)$_{1-6}$—NH—CO—(CH$_2$)$_{1-4}$—, —CO—(CH$_2$)$_{1-6}$—CO—NH—(CH$_2$)$_{1-4}$—, —CO—(CH$_2$)$_{1-6}$—O—(CH$_2$)$_{2-6}$—, —(CH$_2$)$_{2-6}$—, —(CH$_2$)$_{2-6}$—O—(CH$_2$)$_{2-6}$—, —(CH$_2$)$_{2-6}$—NH—CO—(CH$_2$)$_{1-4}$—, optionally in the form of the individual enantiomers or optionally diastereomers, mixtures of the individual enantiomers or optionally diastereomers or racemates, optionally in the form of the acid addition salts thereof with pharmacologically acceptable acids.

6. The compound of formula 1 according to claim 1, characterised in that they are in the form of one of the acid addition salts thereof with pharmacologically acceptable acids, which is selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate.

7. The compound of formula 1 according to claim 1, characterised in that they are in the form of the R-enantiomers of general formula R-1

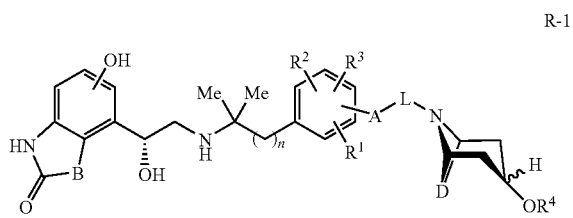

R-1 optionally in the form of the acid addition salts thereof with pharmacologically acceptable acids.

8. The compound of formula 1 according to claim 1, characterised in that they are in the form of the regioisomers of general formula Regio-1a

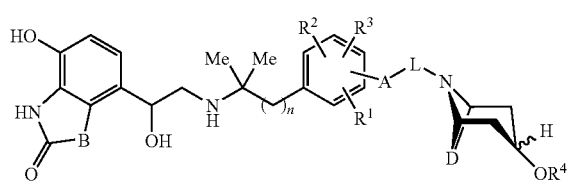

Regio-1a optionally in the form of the individual enantiomers or optionally diastereomers, mixtures of the individual enantiomers or optionally diastereomers or racemates, optionally in the form of the acid addition salts thereof with pharmacologically acceptable acids.

9. The compound of formula 1 according to claim 1, characterised in that they are in the form of the regioisomers of general formula Regio-1b

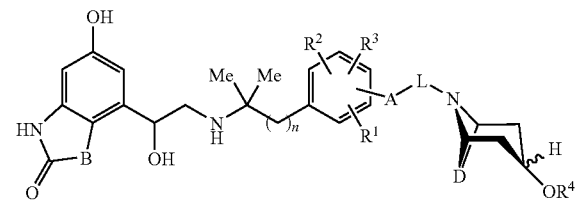

Regio-1b optionally in the form of the individual enantiomers or optionally diastereomers, mixtures of the individual enantiomers or optionally diastereomers or racemates, optionally in the form of the acid addition salts thereof with pharmacologically acceptable acids.

10. A pharmaceutical composition comprising a compound of formula 1 according to claim 1 and a pharmaceutically acceptable carrier or excipient thereof.

11. A pharmaceutical formulation, characterised in that it contains a compound of formula 1 according to claim 1.

12. An intermediate product of formula 7

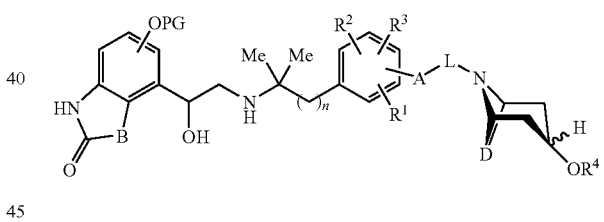

7 wherein

X denotes chlorine, bromine, iodine, methanesulphonate, trifluoromethanesulphonate, p-toluenesulphonate, or an amino function protected by a suitable protective group, preferably —NH—Boc, —NH-Cbz, —NH-Fmoc, —NH-Teoc, or —NH-Alloc;

OPG denotes a hydroxy function protected by a protective group PG, preferably —O—C$_1$-C$_4$-alkyl, —O-benzyl or —O—CH$_2$—O—C$_1$-C$_4$-alkyl, preferably —O-methyl, —O-ethyl, —O-benzyl or —O—CH$_2$—O-methyl, particularly preferably —O-ethyl or —O-benzyl, particularly preferably —O-benzyl; and n, A, L, D, R$^1$, R$^2$ and R$^3$ may have the meanings given in claim 1.

* * * * *